(12) United States Patent
Woehr

(10) Patent No.: US 7,637,887 B2
(45) Date of Patent: Dec. 29, 2009

(54) PROTECTION DEVICE FOR AN INJECTION NEEDLE WITH A CURVED TIP

(75) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 1006 days.

(21) Appl. No.: 10/468,174

(22) PCT Filed: Feb. 15, 2002

(86) PCT No.: PCT/EP02/01659

§ 371 (c)(1),
(2), (4) Date: Feb. 27, 2004

(87) PCT Pub. No.: WO02/066104

PCT Pub. Date: Aug. 29, 2002

(65) Prior Publication Data

US 2004/0138628 A1 Jul. 15, 2004

(30) Foreign Application Priority Data

Feb. 16, 2001 (DE) .......................... 201 02 760 U

(51) Int. Cl.
*A61M 5/00* (2006.01)

(52) U.S. Cl. ..................................... 604/110

(58) Field of Classification Search ................. 604/110, 604/198, 263, 187, 197, 576, 192
See application file for complete search history.

(56) References Cited

U.S. PATENT DOCUMENTS

| 4,929,241 A | * | 5/1990 | Kulli ........................... 604/263 |
| 5,135,504 A | * | 8/1992 | McLees ................. 604/164.08 |
| 5,167,640 A | * | 12/1992 | Balding ...................... 604/192 |
| 5,344,408 A | * | 9/1994 | Partika ........................ 604/192 |
| 5,662,610 A | * | 9/1997 | Sircom ........................ 604/110 |
| 5,951,522 A | * | 9/1999 | Rosato et al. ................ 604/177 |
| 6,203,527 B1 | * | 3/2001 | Zadini et al. ................ 604/110 |
| 6,210,373 B1 | * | 4/2001 | Allmon ....................... 604/192 |
| 6,585,704 B2 | * | 7/2003 | Luther et al. ................ 604/263 |

FOREIGN PATENT DOCUMENTS

WO  WO 99/08742  2/1999

* cited by examiner

*Primary Examiner*—Nicholas D Lucchesi
*Assistant Examiner*—Theodore J Stigell
(74) *Attorney, Agent, or Firm*—Klein, O'Neill & Singh, LLP

(57) ABSTRACT

A protection device for a needle with a curved tip (7) is provided, comprising a tubular part (20) which can be moved along the needle shank (6) and from which at least one elastic arm (30) protrudes in the axial direction in such a way that the free end of said arm bears, with pretensioning, on the needle shank and, upon reaching the needle tip, engages over and covers the latter, said tubular part (20) being configured in such a way that it cannot be pushed over the curved needle tip (7).

21 Claims, 1 Drawing Sheet

PROTECTION DEVICE FOR AN INJECTION NEEDLE WITH A CURVED TIP

CROSS-REFERENCE TO RELATED APPLICATIONS

This application claims priority of International Application No. PCT/EP02/01659, filed Feb. 15, 2002, entitled PROTECTION DEVICE FOR AN INJECTION NEEDLE WITH A CURVED TIP, which claims the benefit of German Application No. 201 02 760.7, filed Feb. 16, 2001, the contents of which is expressly incorporated herein by reference.

SUMMARY OF THE INVENTION

The invention relates to a protection device for an injection needle with a curved tip, for example an epidural needle, a Huber needle or the like.

For giving injections, it is known in the medical field to use what are called Huber needles whose tip is slightly curved so that the mouth of the hollow needle lying obliquely with respect to the needle axis lies substantially parallel to the needle axis. In this way it is possible to introduce the injection needle into part of a patient's body through a fabric, without the open needle tip becoming clogged by the material of the fabric, because the plane of the needle mouth lies in the axial direction of the needle, which direction corresponds to the injection direction.

Moreover, it is known to provide injection needles with a protection device by means of which the needle tip is covered after the needle has been withdrawn from a patient's skin, so that the person giving the injection cannot be injured by the needle tip, thereby avoiding infection, for example by hepatitis or AIDS. In the case of straight injection needles, various designs of protection devices used for this purpose are known.

The object of the invention is to provide a protection device for a needle with a curved tip, which device is of simple construction and in particular can be easily produced.

According to the invention, this object is achieved by the features described in the claims. By providing a tubular portion which can be moved along the needle shank and from which at least one elastic arm protrudes in the axial direction of the needle in such a way that said arm bears, with pretensioning, on the needle shank and, upon reaching the needle tip, engages over and covers the latter, this needle protection device can be easily produced from, for example, a strip of metal, for instance by punching our and bending.

BRIEF DESCRIPTION OF THE DRAWINGS

Illustrative embodiments of the invention are explained in more detail below with reference to the drawings, in which.

DETAILED DESCRIPTION OF THE INVENTION

Figure 1A:
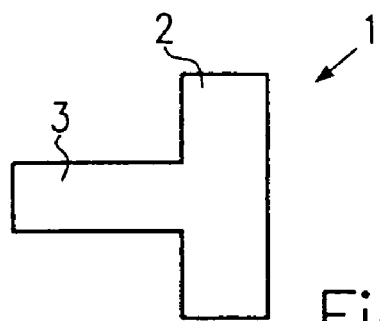
FIG. 1a is a semi-schematic plan view of a punched-out sheet of metallic material for constructing a protective device provided in accordance with aspects of the present invention.

FIG. 1a shows, in a plan view a flat piece 1 which has been punched out from a sheet of metal and is, for example, approximately T-shaped with an approximately rectangular portion 2 from which a likewise approximately rectangular portion 3 protrudes approximately at right angles.

Figure 1B:
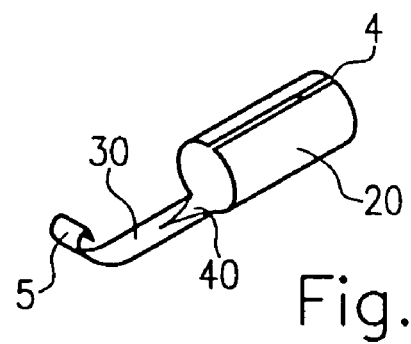
FIG. 1b is a protective device formed from the punched-out sheet of metallic material of FIG. 1a, FIG. 2a is a semi-schematic plan view of an alternative punched-out sheet of metallic material for constructing an alternative protective device provided in accordance with aspects of the present invention.

FIG. 1b shows the protection device which has been formed from this flat piece 1 and in which the rectangular portion 2 is bent to form a tubular part 20 so that the end edges of the portion 2 lie opposite one another along a gap 4. The elastic arm 30, formed by the portion 3, of the protection device has an end 5 which is curved or angled in relation to the longitudinal axis of the tubular part 20 and whose edge is preferably bent inward. This configuration of the arm 30 with curved end 5 can be preformed, during the punching operation, by shaping in a punch mold before the portion 2 is made tubular.

Figure 2A:
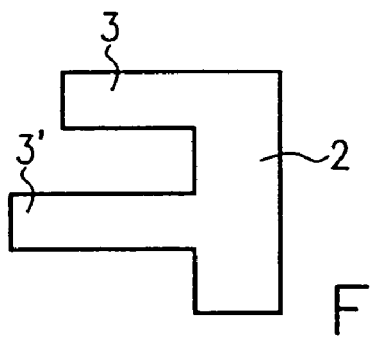
FIG. 2b is a protective device formed from the punched-out sheet of metallic material of FIG. 2a, FIG. 3 shows the arrangement of the protection device according to FIG. 2 on a needle.

FIG. 2a shows a flat piece 1 from whose rectangular portion 2 two portions 3 and 3' protrude approximately at right angles, at a distance from one another. Here, the portion 3' is slightly longer than the portion 3. Moreover, in this illustrative embodiment, the portion 3 is designed in continuation of the end face of the rectangular portion 2.

Figure 2B:
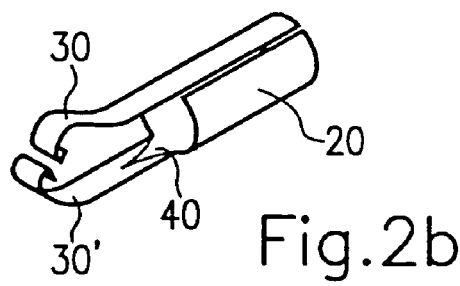

A protection device formed from this flat piece is represented in FIG. 2b. The distance between the two portions 3 and 3' is chosen in such a way that, after the portion 2 has been bent to give a tubular part 20, the portions forming the arms 30 and 30' of the protection device lie diametrically opposite one another. In this configuration too, the free ends of the arms are preferably curved inward, said free ends of the arms 30 and 30' being offset relative to one another as a result of the different length of the corresponding portions of the flat piece 1, as can also be seen from FIGS. 3 and 4.

The arms 30 of the protection device are of planar configuration. FIGS. 1b and 2b show a transition area 40 from the curvature of the tubular part 20 to the flat arm 30, since only a flat arm is elastic in the radial direction, so that the arm can bear with pretensioning on the needle shank and, on reaching the needle tip, can spring back into the protection position, as is illustrated in FIGS. 3 and 4.

Figure 3:
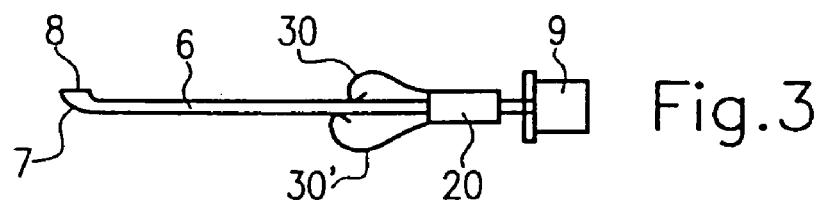
Figure 4:
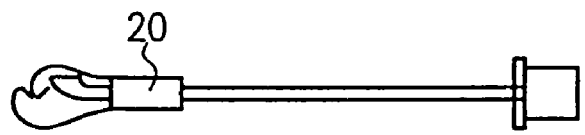
FIG. 4 shows the protection device in the protection position on the needle tip.

FIG. 3 shows the protection device 1 according to FIG. 2b on the shank 6 of the needle, which has a curved tip such that the plane of the mouth 8 lies substantially parallel to the longitudinal axis of the needle. At the opposite end of the needle there is a cannula attachment 9 via which the needle can be fitted to a syringe. The tubular part 20 of the protection device can be moved along the needle shank 6, and the arms 30 and 30' lying opposite one another bear with elastic pretensioning on the needle shank. The internal diameter of the tubular part 20 is chosen in relation to the external diameter of the needle shank 6 so that the protection device an be easily moved along the needle shank 6 but cannot be pushed over the curved tip 7. In the starting position according to FIG. 3, the protection device is expediently situated in the area of the cannula attachment 9. When the needle is withdrawn from the patient's skin after an injection has been given, the protection device can be held in one hand via the tubular part 2, while the needle is pulled back using the other hand. In so doing, the protection device is moved to the protection position represented in FIG. 4, in which position the arms 30 and 30', because of their elastic pretensioning, spring back in the direction toward the needle axis and in so doing cover the needle tip. As a result of the different length of the arms, their free ends engage over one another, so that the needle tip is covered and the risk of injury excluded.

In this protection position or covered position, the protection device can no longer be moved back to the starting position in FIG. 3, because the inwardly angled or rounded ends of the arms engage over the needle tip and prevent rearward movement. Moreover, the protection device cannot be moved beyond the needle tip because the tubular part 20 is configured in such a way that it cannot be pushed over the curved tip 7.

Various modifications of the described embodiments are possible. Thus, the end edges of the portion 2 of a flat piece 1 can also overlap or bear on one another after they have been bent to give a tubular part 20.

Figure 5:
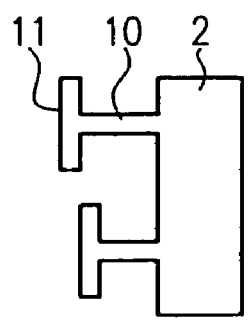
FIG. 5 shows a further embodiment of a punched part.

FIG. 5 shows a modified embodiment in which the portions of the flat piece 1 which form the arms 30 of the protection device are designed in an approximate T-shape with a narrow bridge 10 issuing from the portion 2 and with a widened head portion 11 at the free end. During production, the narrow bridge portion 10 facilitates an elastic design of the arm, while the portion 2 of the flat piece 1 is bent to give the tubular part 20. Here, once again, the two arms are expediently designed with different lengths in order to ensure that they reliably engage over the needle tip.

According to a further embodiment, three arms can also be provided, offset relative to one another in the circumferential direction, on the circumference of the tubular part 20, in which case three portions 3 issuing at intervals from the portion 2 are provided on a flat piece 1.

Upon assembly, the protection device 1 can be pushed onto the end remote from the tip before the cannula attachment 9 is applied.

The flat pieces 1 represented in FIGS. 1, 2 and 5 can also have arm portions 3 and 10 issuing obliquely from the rectangular portion 2, in which case the two arms can be fitted obliquely in opposite directions.

The flat pieces 1 forming a protection device can be easily and quickly produced for example from a metal strip by punching and subsequent shaping. It is also possible to produce a protection device 10 with a tubular portion 20 and with at least one arm 30 formed integrally thereon, for example by injection-molding from a suitably stiff and elastic synthetic material.

What is claimed is:

1. A hypodermic needle assembly comprising a protection device for a hypodermic needle, said protection device comprising a substantially rectangular portion having two sides and two ends rolled into a tubular portion with a gap between the two ends and defining an axis, a first arm and a second arm extending from one of the two sides of the tubular portion and integral with the tubular portion: wherein the first arm and the second arm each comprises a curved end and wherein the curved end of the first arm extends distally of the curved end of the second arm; and wherein the hypodermic needle comprises a needle shaft defining a needle axis and a needle tip; and wherein the tubular portion is coaxially disposed over the needle shaft of the hypodermic needle and the first arm and the second arm of the protection device are biased towards the needle shaft and contact the needle shaft in a ready to use position.

2. The hypodermic needle assembly of claim 1, wherein the hypodermic needle is a Huber needle or an epidural needle.

3. The hypodermic needle assembly of claim 1, wherein the first arm comprises a length that is longer than a length of the second arm.

4. The hypodermic needle assembly of claim 1, further comprising an arcuate transition area positioned intermediate the tubular portion and the arm.

5. The hypodermic needle assembly of claim 1, wherein the first arm or the second arm comprises an edge, the edge being coplanar with one of the ends of the tubular portion.

6. The hypodermic needle assembly of claim 1, wherein the tubular portion comprises an inside dimension sized to abut a curved needle portion of the needle shaft when the tubular portion is moved distally in the direction of the needle tip.

7. The hypodermic needle assembly of claim 1, wherein the protection device is stamped from a flat metal sheet.

8. The hypodermic needle assembly of claim 1, wherein at least one of the first arm and the second arm of the protection device comprises a widened head portion having a width larger than a width of the arm.

9. The hypodermic needle assembly of claim 1, wherein the tubular portion abuts a curved needle portion of the needle shaft and the curved ends of the first and second arms extend distally of the needle tip in an overlapping configuration.

10. A hypodermic needle assembly comprising a protection device disposed over a shaft of a hypodermic needle comprising a curved tip; wherein:
    the protection device comprises a tubular portion comprising two ends and a gap therebetween, which is generally parallel to the shaft of the needle, and an arm extending transversely or obliquely from at least one of the two ends and integral with the tubular portion;
    a first maximum diameter defined by a circumferential surface of the tubular portion; and
    wherein the tubular portion is axially disposed over the shaft of the hypodermic needle and the arm is biased towards the shaft with a portion of the arm abutting the shaft in a ready to use position.

11. The hypodermic needle assembly of claim 10, wherein the protection device is made from stamped metal sheet and shaped by bending at least a portion of the stamped metal sheet.

12. The hypodermic needle assembly of claim 10, wherein the protection device is made by injection molding a synthetic material.

13. The hypodermic needle assembly of claim 10, wherein the arm of the protection device comprises a curved end.

14. The hypodermic needle assembly of claim 10, wherein the hypodermic needle is a Huber needle or an epidural needle.

15. The hypodermic needle assembly of claim 10, further comprising a second arm extending transversely or obliquely from the at least one of the two ends.

16. The hypodermic needle assembly of claim 15, wherein the first arm and the second arm are diametrically opposed to one another and the hypodermic needle is disposed between the first and second arms.

17. The hypodermic needle assembly of claim 15, wherein the first arm comprises a length that is longer than a length of the second arm.

18. The hypodermic needle assembly of claim 17, wherein the first arm and the second arm each comprises a curved end.

19. The hypodermic needle assembly of claim 15, wherein the first arm or the second arm comprises an edge, the edge being coplanar with one of the ends of the tubular portion.

20. The hypodermic needle assembly of claim 10, wherein the arm comprises a widened head portion having a width larger than a width of the arm.

21. A hypodermic needle assembly comprising a safety device coaxially disposed over a shaft of a hypodermic needle comprising a needle tip having a bend; the safety device comprising an arm and a curved section formed at a distal end thereof integrally formed to and extending from a tubular portion of the safety device, the arm is resiliently biased towards the shaft of the hypodermic needle and the curved section is abutted against a side of the shaft; and wherein the tubular portion of the safety device comprises an opening comprising a dimension sized to be obstructed by the bend of the needle when the safety device moves from a proximal position to a distal position on the shaft.

* * * * *